(12) United States Patent
Pabbaraja et al.

(10) Patent No.: US 11,802,112 B2
(45) Date of Patent: Oct. 31, 2023

(54) CONTINUOUS FLOW MICRO-TOTAL PROCESS SYSTEM FOR PREPARATION OF CELECOXIB AND ANALOGS THEREOF

(71) Applicant: Council of Scientific and Industrial Research, New Delhi (IN)

(72) Inventors: Srihari Pabbaraja, Telangana (IN); Ajay Kumar Singh, Telangana (IN); Vinay Kumar Sthalam, Telangana (IN)

(73) Assignee: Council of Scientific & Industrial Research, New Delhi (IN)

( * ) Notice: Subject to any disclaimer, the term of this patent is extended or adjusted under 35 U.S.C. 154(b) by 133 days.

(21) Appl. No.: 17/426,906

(22) PCT Filed: Jan. 27, 2020

(86) PCT No.: PCT/IN2020/050088
§ 371 (c)(1),
(2) Date: Jul. 29, 2021

(87) PCT Pub. No.: WO2020/157771
PCT Pub. Date: Aug. 6, 2020

(65) Prior Publication Data
US 2022/0127235 A1    Apr. 28, 2022

(30) Foreign Application Priority Data
Feb. 1, 2019   (IN) .............................. 201911004015

(51) Int. Cl.
*C07D 231/12*   (2006.01)
(52) U.S. Cl.
CPC ................................. *C07D 231/12* (2013.01)
(58) Field of Classification Search
CPC .................................................. C07D 231/12
See application file for complete search history.

(56) References Cited

U.S. PATENT DOCUMENTS

2008/0023449 A1    1/2008  Salsich et al.

FOREIGN PATENT DOCUMENTS

WO    2010095024 A2    8/2010

OTHER PUBLICATIONS

International Search Report in reference to co-pending Indian Patent Application No. PCT/IN2020/050088 filed Jan. 27, 2020.
Written Opinion dated Jan. 5, 2020 in reference to co-pending Indian Patent Application No. PCT/IN2020/050088 filed Jan. 27, 2020.
Reddy, et al., "An Improved and Scalable Process for Celecoxib: A Selective Cyclooxygenase-2 Inhibitor", Organic Press Research & Development, vol. 13, pp. 98-101, Dec. 2009.
Britton, et al., "A Unified Continuous Flow Assembly-Line Synthesis of Highly Substituted Pyrazoles and Pyrazolines", Angew. Chem., vol. 129, pp. 8949-8953, 2017.
Thombal, et al., "Synergistic Indium and Silver Dual Catalysis: A Regioselective [2 + 2 + 1]-Oxidative N-Annulation Approach for the Diverse and Polyfunctionlized N-Arylpyrazoles", Organic Letters, vol. 20, pp. 4681-4685, 2018.
Wang, et al., "Cascade Oxidation/Halogenoaminocyclization Reaction of Trifluoromethylated Homoallylic N-Acylhydrazines: Metal-free Synthesis of $CF_3$-Substituted Pyrazolines", The Journal of Organic Chemistry, vol. 83, pp. 939-950, 2018.
Kamal, et al., "One-Pot Three-Component Approach to the Synthesis of 3,4,5 Trisubstituted Pyrazoles", The Journal of Organic Chemistry, vol. 80, pp. 4325-4335, 2015.
Reddy, et al., "Facile One-Pot Synthesis of 3,5-Disubstituted 1H-Pyrazoles from Propargylic Alcohols via Propargyl Hydrazides", Synthesis, vol. 45, pp. 830-836, 2013.
Garg, et al., "Cyclooxygenase (COX) Inhibitors: A Comparative QSAR Study", Chem. Rev. vol. 103, pp. 703-731, 2003.
Szabó, et al., "New Celecoxib Derivatives as Anti-Inflammatory Agents", Journal Med. Chem., vol. 51, pp. 142-147, 2008.
Penning, et al., "Synthesis and Biological Evaluation of the 1,5-Diarylpyrazole Class of Cyclooxygenase-2 Inhibitors: Identitification of 4-[5-(4-Methylphenyl)-3-(trifluoromethyl)-1H-pyrazol-1-yl]benzenesulfonamide (SC-58635, Calecoxib)", Journal Med. Chem., vol. 40, pp. 1347-1365, 1997.
Lill, et al., "Synthesis of novel dansyl-labeled Celecoxib derivatives", Tetrahedron Letters, vol. 54, pp. 6682-6686, 2013.
Abdellatif, et al., "Diazen-1-ium-1,2-diolated nitric oxide donor ester prodrugs of 5-(4-hydroxymethylphenyl)-1-(4-aminosulfonylphenyl)-3-trifluoromethyl-1H-pyrazole and its methanesulfonyl analog: Synthesis, biological evaluation and nitric oxide release studies", Bioorganic & Medicinal Chemistry, vol. 16, pp. 9694-9698, 2008.
Gao, et al., "Synthesis and preliminary in vitro biological evaluation of new carbon-11-labeled celecoxib derivatives as candidate PET tracers for imaging of COX-2 expression in cancer", European Journal of Medicinal Chemistry, vol. 46, pp. 4760-4767, 2011.
Jeong, et al., "One-flpw synthesis of diverse heterocyclic furan chemicals directly from fructose via tandem transformation platform", NPG Asia Materials, vol. 7, pp. 1-8, 2015.
Sharma, et al., "Odorless Isocyanide Chemistry: An Integrated Microfluidic System for a Multistep Reaction Sequence", Angew. Chem., vol. 125, pp. 7712-7716, 2013.

*Primary Examiner* — Shawquia Jackson
(74) *Attorney, Agent, or Firm* — DINSMORE & SHOHL, LLP

(57) ABSTRACT

The present invention relates to preparation of pyrazoles. This invention further relates to a continuous flow micro-total process system for preparation of celecoxib, a COX-2 selective non-steroidal anti-inflammatory drug, and analogs thereof.

9 Claims, 4 Drawing Sheets

CONTINUOUS FLOW MICRO-TOTAL PROCESS SYSTEM FOR PREPARATION OF CELECOXIB AND ANALOGS THEREOF

CROSS REFERENCES TO RELATED APPLICATIONS

This application is a national-stage application under 35 U.S.C. § 371 of International Application No. PCT/IN2020/050088, filed Jan. 27, 2020, which International Application claims benefit of priority to Indian Application No. 201911004015, filed Feb. 1, 2019.

FIELD OF THE INVENTION

The present invention relates to a continuous flow micro-total process system for the preparation of celecoxib and analogs thereof of following Formula I, wherein 'R' is a substituted phenyl or heterocyclic substituent.

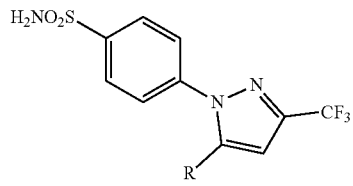

(I)

This invention further relates to the said process for preparation of COX-2 selective non-steroidal anti-inflammatory drug, celecoxib.

BACK GROUND OF THE INVENTION

The present protocol focuses on the synthesis of pyrazoles which have been of a great interest since long time in the history of natural products/pharmaceutical therapeutic agents, including biologically active compounds like anti-inflammatory, anti-diabetics, and have been used in all areas of academia as well as industry (*Organic Process Research & Development* 13, 98-101 (2009); *Angewandte Chemie International Edition* 56, 8823-8827 (2017); *Organic Letters* 20, 4681-4685 (2018); *The Journal of Organic Chemistry* 83, 939-950 (2018); *The Journal of Organic Chemistry* 80, 4325-4335 (2015); *Synthesis* 45, 830-836 (2013); *Chemistry Letters* 37, 624 (2008)).

Celecoxib is a selective non-steroidal anti-inflammatory drug (NSAID) belonging to a family of non-arylamine benzene sulfonamide derived cyclooxygenase-2 (COX-2) inhibitors; that can be dosed for the treatment of many human diseases (e.g., osteoarthritis, painful menstruation, acute pain and rheumatoid arthritis) in addition to cancer (*Chemical Reviews* 103, 703-732 (2003).

Cyclooxygenase-2 (COX-2) derivative was prepared conventionally (in batch process) by the condensation of a diketone substrates with the corresponding aromatic hydrazine's using ethanol or water as solvent under the heating condition (*Journal of Medicinal Chemistry* 51, 142-147 (2008); *Journal of Medicinal Chemistry* 40, 1347-1365 (1997); *Tetrahedron Letters* 54, 6682-6686 (2013); *Bioorganic & Medicinal Chemistry* 16, 9694-9698 (2008)).

Though the batch reaction works rationally well, insufficient surface-to-volume ratio and heat transfer make the system a limited scope process, having drawbacks, such as (a) longer reaction time (20 h), (b) improper mixing and usage of mixture of solvents for purification, (c) a relatively more amount of regioisomer impurity (0.5%) due to the mixing problem, and (d) usage of a multisolvent system, making the reaction system less feasible for commercial production (*Organic Process Research & Development* 13, 98-101 (2009); *European Journal of Medicinal Chemistry* 46, 4760-4767 (2011)).

Nevertheless, many batch process reactions in general result off quality product due to the repetition of stop and start up action to attain completion or conversion. Several unit operations required like tanks, vessels, funnels cannot be left with materials because of unwanted chemical reactions, hardening of materials, settling of suspended materials or crystallization that further makes the method more tedious.

During the shutting down and starting up cycling of temperatures and pressures of celecoxib synthesis processes (blast furnaces, pressure vessels, line kilns, boilers and pipes etc.) might cause contamination of metal impurity or other impurities like by-products. Additionally, the purification of celecoxib derivative is highly laborious.

In the recent past, an emerging technology so called continuous-flow micro fluidic device is an efficient synthetic tool which can overcome the issues related to batch processes with an attractive advantage such as an excellent mass and heat transfer, high surface-to-volume ratio, which leads to an enrichment in the selectivity and a reduction in reaction time (*Npg Asia Materials* 7, e173 (2015); *Angewandte Chemie* 125, 7712-7716 (2013)). In addition, micro-total process system (μ-TPS) involving the workup streams like quenching, extraction and separation system does not require any additional aqueous workup or column chromatography, which totally remove the tedious issues related to the celecoxib synthesis processes (*Korean Journal of Chemical Engineering* 33, 2253-2267 (2016)).

To employ the concept of a total process in this paradigm, herein the applicant provide an efficient, improved, simple, economical and scalable process for the micro-total process system (μ-TPS) platform consisting of micro fluidic system which enable the generation of the selective celecoxib, its separation, analysis and purification from the reaction products. The applicant has also outlined the initial challenges, faced during the early μ-TPS campaigns, and consequently addressed the celecoxib production even on a large laboratory scale.

OBJECTIVE OF THE INVENTION

In view of the limitations in the prior art, the main objective of the present invention is to provide a continuous flow micro-total process system for preparation of celecoxib and analogs thereof.

Another objective of the present invention is to provide a process that can be carried out in continuous flow micro-total process system for preparation of celecoxib, a COX-2 selective non-steroidal anti-inflammatory drug.

SUMMARY OF THE INVENTION

In an embodiment, the present invention provides a continuous flow micro-total process system for the preparation of celecoxib and analogs thereof of following Formula I, wherein "R' is a substituted phenyl or heterocyclic group substituted with one or more substituents selected from the group consisting of: halogen, hydroxy, alkoxy, aldehyde, carboxylic acid, nitro, alkyl, amino, thiol and ester.

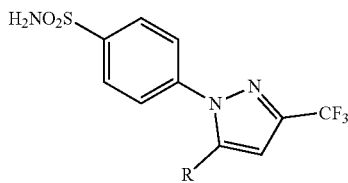
(I)

In another embodiment, the representative compounds of Formula I are:

4-(5-p-tolyl-3-(trifluoromethyl)-1H-pyrazol-1-yl)benzene sulfonamide (3a); 4-(5-phenyl-3-(trifluoromethyl)-1H-pyrazol-1-yl)benzene sulfonamide (3b); 4-(5-(4-fluorophenyl)-3-(trifluoromethyl)-1H-pyrazol-1-yl)benzene sulfonamide (3c); 4-(5-(4-chlorophenyl)-3-(trifluoromethyl)-1H-pyrazol-1-yl)benzene sulfonamide (3d); 4-(5-(4-bromophenyl)-3-(trifluoromethyl)-1H-pyrazol-1-yl)benzene sulfonamide (3e); 4-(5-(4-methoxyphenyl)-3-(trifluoromethyl)-1H-pyrazol-1-yl)benzene sulfonamide (3f); 4-(5-(biphenyl-4-yl)-3-(trifluoromethyl)-1H-pyrazol-1-yl)benzene sulfonamide (3g); 4-(5-(4-nitrophenyl)-3-(trifluoromethyl)-1H-pyrazol-1-yl)benzene sulfonamide (3h); and 4-(5-(thiophen-2-yl)-3-(trifluoromethyl)-1H-pyrazol-1-yl)benzene sulfonamide (3i).

In yet another embodiment, the present invention provides a continuous flow micro-total process system for the preparation of celecoxib and analogs thereof of Formula I, wherein 'R' is a substituted phenyl or heterocyclic group substituted with one or more substituents selected from the group consisting of: halogen, hydroxy, alkoxy, aldehyde, carboxylic acid, nitro, alkyl, amino, thiol and ester; comprising:

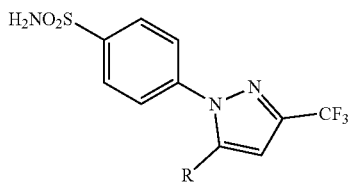
(I)

(i) introducing a solution of reactants of Formula 1 and Formula 2 in a suitable protic solvent and water to a micro-reactor;

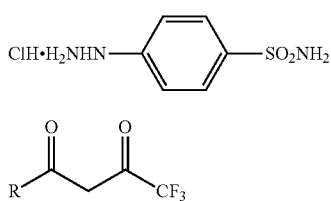
(1)
(2)

(ii) maintaining the reaction mixture of step (i) in microreactor for about 10-30 minutes at a temperature of about 80-130° C. and at a pressure of about 25-35 bar for the synthesis of compounds of Formula I;

(iii) introducing a suitable basifying agent and suitable extraction solvents to reaction mixture of step (ii) to form organic-aqueous droplets;

(iv) separating the organic and aqueous segments by passing through organic-aqueous droplets of step (iii) to micro-separator, in presence of a suitable solvent system;

(v) removing organic solvents to obtain compound of Formula I; and (vi) optionally, purifying compound of Formula I In another embodiment, the present invention provides use of a continuous flow micro-total process system for the preparation of celecoxib and analogs thereof of Formula I.

In yet another embodiment, the present invention provides a process for the preparation of celecoxib and analogs thereof of Formula I involving a continuous flow micro-total process system.

DETAILED DESCRIPTION OF THE INVENTION

Figure 1:
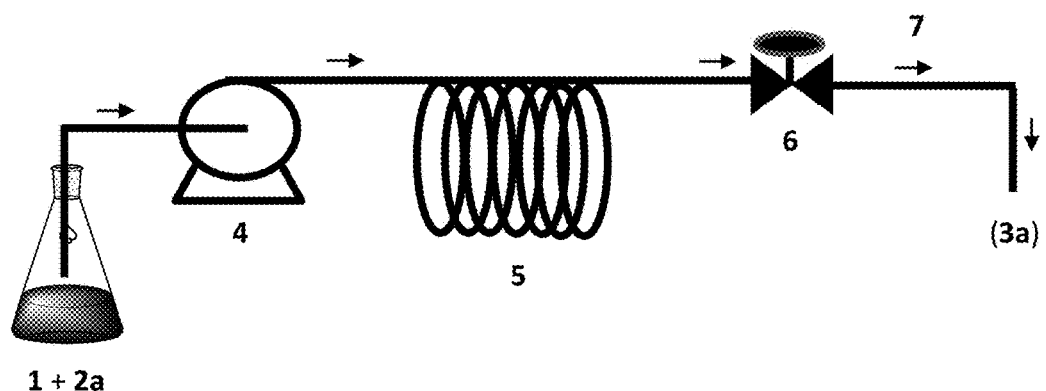
FIG. 1: Illustration of a basic set-up of the continuous flow synthesis reactor employed in the synthesis of celecoxib (3a) using micro-reaction technology.

The present invention provides new procedures and technology for the preparation of pyrazoles of Formula I, preferably Celecoxib and analogs thereof.

The present invention further encompasses novel continuous flow micro-total process system for preparation of celecoxib and analogs thereof.

As discussed earlier, the processes described in the prior-art, which are mostly batch processes, have significant disadvantages.

In contrast to the prior art processes, the present invention provides an efficient, improved, simple, economical and scalable new process for the micro-total process system (μ-TPS) platform consisting of micro fluidic system which enable the generation of the selective celecoxib and analogs of Formula I, its separation, analysis and optionally purification from the reaction products. The total process of the present invention can be easily extended to other pyrazole synthesis system, multi-step reaction, and for toxic or noxious chemicals. More importantly, the integrated continuous flow platform of the present invention would enable a future automation of laboratory and industry to produce on-demand pyrazoles in the areas of drug discovery, natural products, materials synthesis etc.

As used herein, the modifier "about" should be considered as disclosing the range defined by the absolute values of the two endpoints. For example, the expression "from about 1 to about 4" also discloses the range "from 1 to 4." When used to modify a single number, the term "about" may refer to ±10% of the said number including the indicated number. For example, "about 10%" may cover a range of 9% to 11%, and "about 1" means from 0.9-1.1.

As used herein, the term "reduced pressure" refers to a pressure that is less than atmospheric pressure. For example, the reduced pressure is about 10 mbar to about 50 mbar.

As used herein, the term "pump" refers to a device that moves fluids (liquids or gases), or sometimes slurries, by mechanical action.

As used herein, the term "protic solvents" refers to any organic solvent that contains a labile $H^+$.

In an embodiment, the present invention provides a continuous flow micro-total process system for the preparation of celecoxib and analogs thereof of following Formula I, wherein 'R' is a substituted phenyl or heterocyclic group substituted with one or more substituents selected from the group consisting of: halogen, hydroxy, alkoxy, aldehyde, carboxylic acid, nitro, alkyl, amino, thiol and ester.

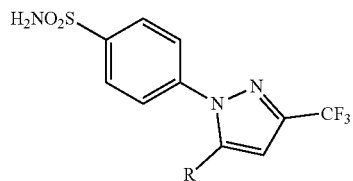

(I)

In another embodiment, the representative compounds of Formula I are:

4-(5-p-tolyl-3-(trifluoromethyl)-1H-pyrazol-1-yl)benzene sulfonamide (3a); 4-(5-phenyl-3-(trifluoromethyl)-1H-pyrazol-1-yl)benzene sulfonamide (3b); 4-(5-(4-fluorophenyl)-3-(trifluoromethyl)-1H-pyrazol-1-yl)benzene sulfonamide (3c); 4-(5-(4-chlorophenyl)-3-(trifluoromethyl)-1H-pyrazol-1-yl)benzene sulfonamide (3d); 4-(5-(4-bromophenyl)-3-(trifluoromethyl)-1H-pyrazol-1-yl)benzene sulfonamide (3e); 4-(5-(4-methoxyphenyl)-3-(trifluoromethyl)-1H-pyrazol-1-yl)benzene sulfonamide (3f); 4-(5-(biphenyl-4-yl)-3-(trifluoromethyl)-1H-pyrazol-1-yl)benzene sulfonamide (3g); 4-(5-(4-nitrophenyl)-3-(trifluoromethyl)-1H-pyrazol-1-yl)benzene sulfonamide (3h); and 4-(5-(thiophen-2-yl)-3-(trifluoromethyl)-1H-pyrazol-1-yl)benzene sulfonamide (3i).

In yet another embodiment, the present invention provides a continuous flow micro-total process system for the preparation of celecoxib and analogs thereof of Formula I, wherein 'R' is a substituted phenyl or heterocyclic group substituted with one or more substituents selected from the group consisting of: halogen, hydroxy, alkoxy, aldehyde, carboxylic acid, nitro, alkyl, amino, thiol and ester; comprising:

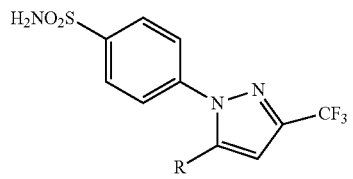

(I)

(i) introducing a solution of reactants of Formula 1 and Formula 2 in a suitable protic solvent and water to a micro-reactor;

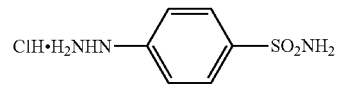

(1)

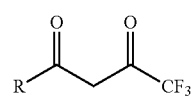

(2)

(ii) maintaining the reaction mixture of step (i) in micro-reactor for about 10-60 minutes at a temperature of about 60-130° C. and at a pressure of about 10-35 bar for the synthesis of compounds of Formula I;

(iii) introducing a suitable basifying agent and suitable extraction solvents to reaction mixture of step (ii) to form organic-aqueous droplets;

(iv) separating the organic and aqueous segments by passing through organic-aqueous droplets of step (iii) to micro-separator, in presence of a suitable extraction solvent system;

(v) removing organic solvents to obtain compound of Formula I; and (vi) optionally, purifying compound of Formula I.

The solution of step (i) may be introduced to the micro-reactor using a pump or by using any other suitable device capable of moving fluids (liquids or gases) or sometimes slurries by mechanical action.

Suitable protic solvents for step (i) include, but are not limited to, alcoholic solvents, or the like. Preferably, the alcoholic solvent is selected from the group consisting of methanol, ethanol, iso-propanol, n-butanol, t-butanol or mixture thereof. Most preferably, the alcoholic solvent is methanol.

Preferably, the reactants of Formula 1 & Formula 2, and protic solvent & water are in a molar ratio of about Formula 1:Formula 2:Protic solvent:Water (1:1:277:45).

Preferably, micro-reactor in step (ii) comprises stainless steel (SS) tubing. Preferably, the SS tubing may have specification: inner diameter (ID) of about 800-1000 μm and length of about 8-15 meter.

Suitable basifying agents in step (iii) include, but are not limited to inorganic bases, or the like. Preferably, the basifying agent is an aqueous solution of bases such as KOH, $Na_2CO_3$, and $NaHCO_3$. Most preferably, the basifying agent is NaOH.

Suitable extraction solvents in step (iii) include but are not limited to hydrophobic solvents, or the like. Suitable extraction solvents may include, for example, polar solvents and non-polar solvents. Preferably, the polar solvent is selected from the group consisting of dichloroethane, chloroform, low boiling dichloromethane, diethyl ether, dimethyl ether, isopropyl ether or mixture thereof. Preferably, the non-polar solvent is selected from the group consisting of toluene, mesitylene, xylene, low boiling hexane or mixture thereof. Most preferably, the suitable extraction solvent is low boiling diethyl ether. Preferably, the solution of reactants of Formula 1 & Formula 2, solvents methanol & water, extracting solvent, and basifying agent are passed through the X junction, which is further connected with fluoropolymer tubing. Preferably, fluoropolymer tubing is made of PFA, PTFE, ETFE, or the like. Most preferably, fluoropolymer tubing is made of PTFE having the specification: inner diameter (ID) of about 800-1000 μm and length of about 1-2 meter.

In the process of separation of the organic and aqueous segments in step (iv); the suitable extraction solvents will wet the thin fluoropolymer membrane and permeate to the opposite channel of the separator, whereas the aqueous phase containing water, MeOH, NaOH and HCl do not wet the membrane and maintained at the original flow.

Preferably, organic solvents in step (v) are removed under reduced pressure.

The method of purification is selected from any suitable method known in the art, which include but is not limited to chromatography technique, distillation, crystallisation etc.

In another embodiment, the present invention provides use of a continuous flow micro-total process system for the preparation of celecoxib and analogs thereof of Formula I.

In yet another embodiment, the present invention provides a process for the preparation of celecoxib and analogs thereof of Formula I involving a continuous flow micro-total process system.

In another embodiment, the representative compounds of Formula 2 are:

4,4,4-trifluoro-1-(p-tolyl) butane-1,3-dione (2a); 4,4,4-trifluoro-1-phenyl butane-1,3-dione (2b); 4,4,4-trifluoro-1-(4-fluorophenyl) butane-1,3-dione (2c); 1-(4-chlorophenyl)-4,4,4-trifluorobutane-1,3-dione (2d); 1-(4-bromophenyl)-4,4,4-trifluorobutane-1,3-dione (2e); 4,4,4-trifluoro-1-(4-methoxyphenyl)butane-1,3-dione (2f); 1-([1,1'-biphenyl]-4-yl)-4,4,4-trifluorobutane-1,3-dione (2g); 4,4,4-trifluoro-1-(4-nitrophenyl) butane-1,3-dione (2h); and 4,4,4-trifluoro-1-(thiophen-2-yl) butane-1,3-dione (2i).

FIG. 1 illustrates a basic set-up of the continuous flow synthesis reactor used in the synthesis of celecoxib (3a) using micro-reaction technology. The reactants of Formula (1) and Formula (2a) are introduced to a micro-reactor (5) using a pump (4). The separation of organic-aqueous segment was achieved by using suitable extraction solvent (7), regulating the backpressures by the use of back pressure regulator (BPR) (6), retention time and flow rate to afford celecoxib (3a). Table 1 describes optimization of synthesis of Celecoxib (3a) synthesis in continuous flow process. In general, reaction performance is found to be dependent on the flow rate (residence time), reactor pressure, temperature, and the concentrations of reactants.

After studying several reaction conditions, finally 85% yield of 3a (0.33 mmol h$^{-1}$ productivity, Table 1, Entry 3) was obtained in 13.3 min, at 120° C. and 32 bar pressure; which is about 90 times faster than batch reaction.

TABLE 1

Optimization of Celecoxib (3a) synthesis in continuous flow process.

| Entry | Flow rate (μL/Min.) (2a) | Retention time (Min.) | % Isolated Yield (3a) |
|---|---|---|---|
| 1$^a$ | 1000 | 8.0 | 78 |
| 2$^a$ | 2000 | 4.0 | 75 |
| 3$^a$ | 600 | 13.3 | 85 |
| 4$^a$ | 500 | 16.0 | 85 |
| 5$^a$ | 50 | 160.0 | 83 |
| 6$^b$ | 600 | 13.3 | NA |
| 7$^c$ | 600 | 13.3 | NA |
| 8$^d$ | 600 | 13.3 | NA |
| 9$^e$ | 600 | 13.3 | NA |
| 10$^f$ | 600 | 13.3 | NA |

Reaction condition: Feed solution molar ratio (2a: 1: MeOH: H$_2$O) (1:1:277:45); SS tubing (ID: 1 mm and length 10.2 meter). (a) pressure 32 bar at 120° C.; (b) pressure 32 bar at 60° C.; (c) pressure 32 bar at 80° C.; (d) pressure 32 bar at 100° C.; (e) pressure 10 bar at 120° C.; and (f) pressure 17 bar at 120° C.

Figure 2:
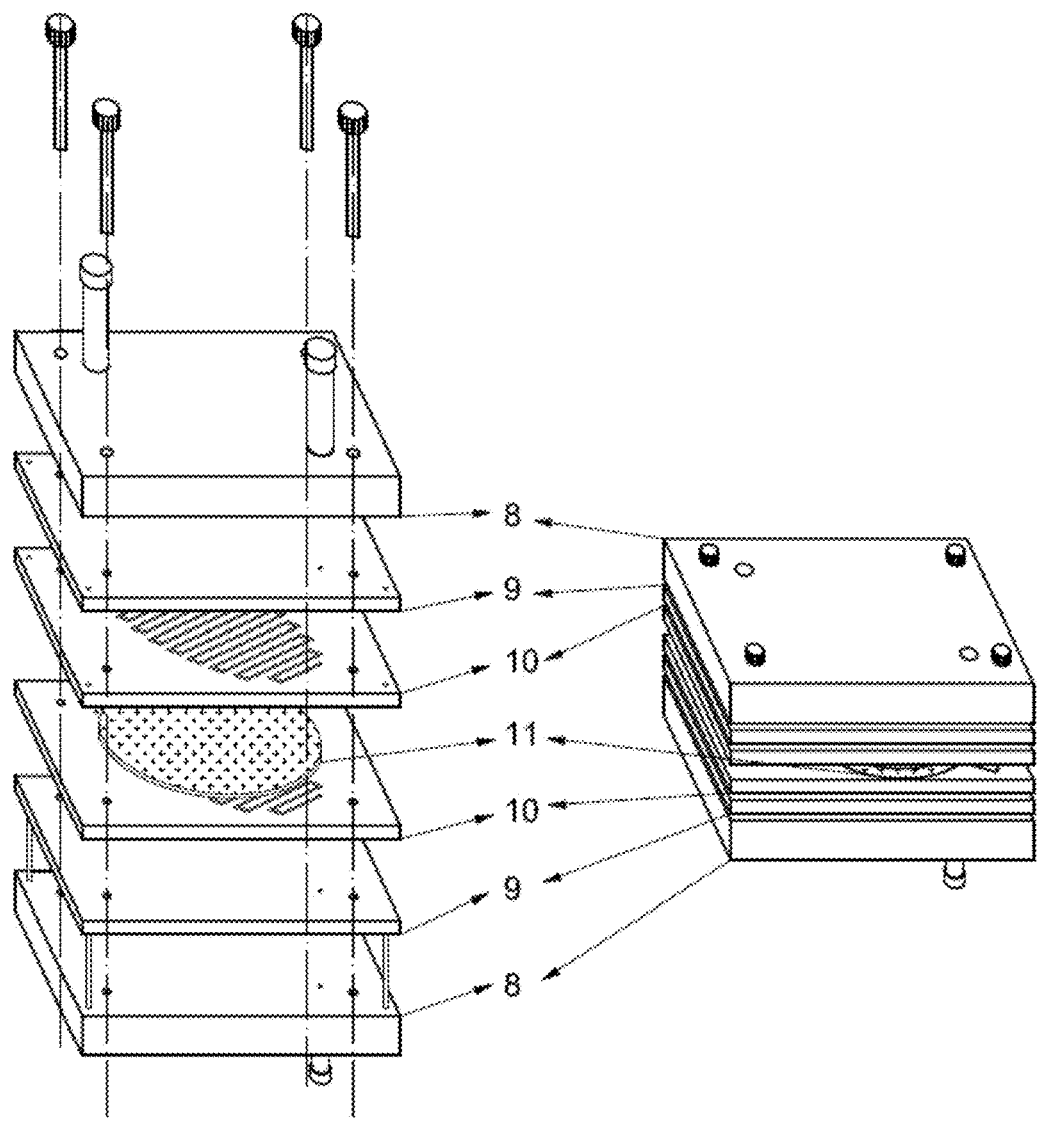
FIG. 2: Illustration of a schematic and original image of liquid-liquid micro-separator with details of inside arrangements.

FIG. 2 is an illustration of a schematic and original image of liquid-liquid micro-separator with details of inside arrangements. The liquid-liquid micro-separator consists of the components viz. metal holder (8), metal protecting PTFE or PE film (9), spiral polymer-based channel (10) and polypropylene coated PTFE porous thin film membrane (11). The design of liquid-liquid micro-separator is targeted to develop the integrated total process strategy including the steps of reaction, quenching, extraction and separation for the selective removal of solvents and aqueous impurity (e.g. salt, acid and bases), chemicals/solvent in order to reduce tedious workup steps [(*European Journal of Organic Chemistry* 2018, 2831-2835 (2018); Nature Communication 8, 14676 (2017); Nature Communications 7, 10741 (2016); *Angewandte Chemie International Edition* 52, 6735-6738 (2013)].

Figure 3:
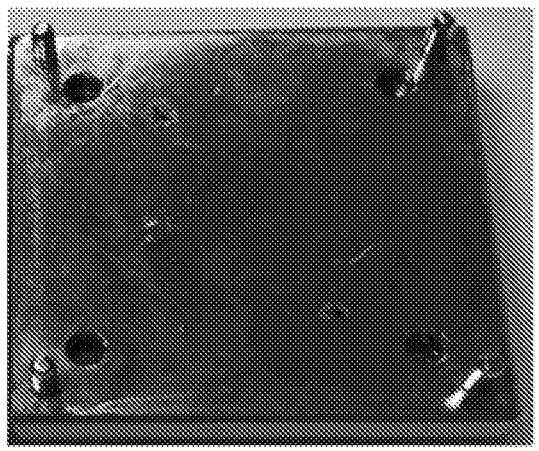
FIG. 3: Metal (SS, Cu, Al etc) holder design of liquid-liquid micro-separator.

FIG. 3 illustrates metal holder (8), a micro separator outer body design. Micro-separator has been fabricated with a stainless-steel body.

Figure 4:
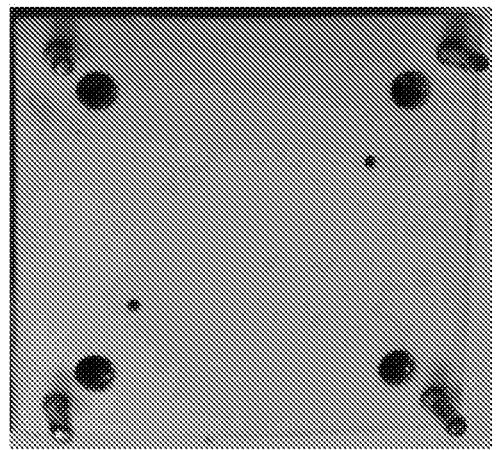
FIG. 4: Laser grooved polytetrafluoroethylene (PTFE) or polyethylene (PE) film for the metal corrosion protection from the acid and bases.

FIG. 4 is an illustration of a metal protecting PTFE or PE film (9), the second layer of micro-separator. Preferably, it is fabricated with teflon (60 mm length×60 mm width×2 mm thickness) layer made with laser cutter for protecting the stainless steel from the corrosive acid base.

Figure 5:
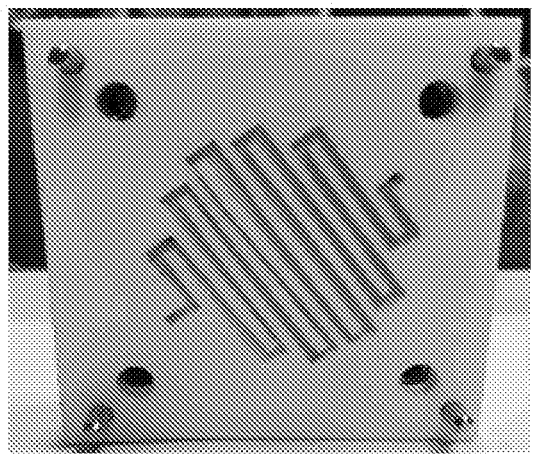
FIG. 5: Laser grooved spiral polymer-based channel for solution flow and mixing efficiency.

FIG. 5 is an illustration of laser grooved spiral polymer-based channel (10), the third layer of micro-separator, for solution flow and mixing efficiency. Preferably, the solution pathway comprises a laser cutted teflon plastic (60 mm×60 mm×2 mm thickness) zig-zag groove with rectangular shape (2 mm×80.0 mm).

Figure 6:
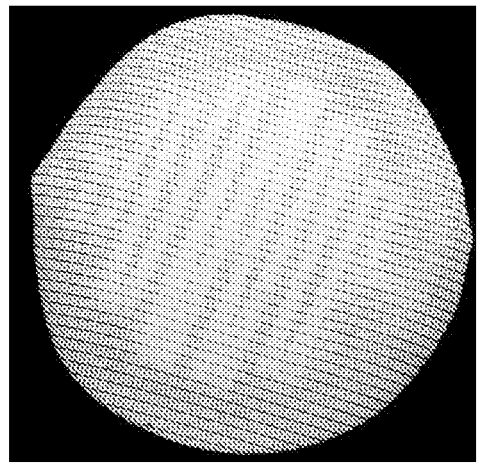
FIG. 6: Polypropylene coated PTFE porous thin film membrane; which is solvent, acid and base resistant.

FIG. 6 illustrates polypropylene coated PTFE porous thin film membrane (11) to make align the film patterns. The 4-corners of each two teflon film are drilled to make a hole (1 mm diameter). Thereafter, a polytetrafluoroethylene (PTFE) membrane (Whatmann, 37 mm dia.) is merged by two teflon sheets with identical dimension to fit groove channels and coupled to each other by inserting metal pins through the holes at the film corners.

Figure 7:
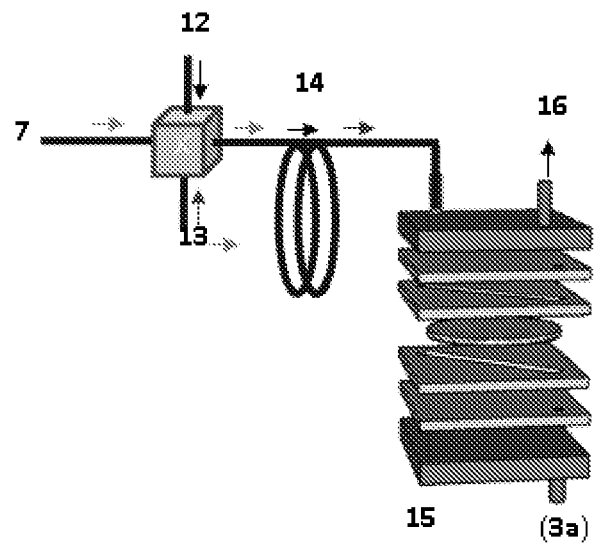
FIG. 7: Illustration of in-line continuous extraction and separation of the first step synthesized celecoxib product.

FIG. 7 is an Illustration of in-line continuous extraction and separation of the first step synthesized celecoxib product. A successive progression of droplet formation, extraction and separation for purification of the Celecoxib (3a) is passed in a droplet microfluidics equipped with the PTFE membrane micro separator. Prior to an integrated continuous one-flow system for various compounds synthesis, the reaction conditions for extraction and separation of celecoxib has been optimised.

At first step, aqueous basic solution (13), preferably NaOH, is introduced into the product mixture along with extracting solvent (12), preferably, dichloromethane (DCM) or Toluene or diethyl ether, through 'X-junction' with the desired flow rate in order to extract the product mixture into the extracting solvent (12). Table 2 describes solvent screening for extraction.

In a second step extraction takes place at 'A-junction' where the suitable protic solvent, preferably MeOH, in the reaction mixture is progressively moved to aqueous droplet phase and real time extraction occurs through extraction section (14), preferably a PTFE capillary (id=1000 μm, length=2.6 m, vol.=2 mL).

Final step product extracted into the organic phase will wet the thin PTFE membrane and permeate to the opposite channel of the micro-separator (15), whereas the aqueous phase containing the waste (16) do not wet the membrane and maintained at the original flow.

After the extensive optimization extraction (0.5 min) and separation process (7.9 sec), it is observed that diethyl ether is the most preferred solvent (Table 2, Entry 13).

In the above described process of the present invention, celecoxib (3a) has been prepared without any workup steps, such as washing of the product or acid base treatment, and even without the requirement to dry the material.

TABLE 2

Solvent screening for extraction using micro-separator.

| Entry | Solvent | Solvent flow rate (mL/min) | Aq. NaOH Sol. flow rate (mL/min) | Extraction time (min.) | Separation time (sec) | % Isolated Yield (3a) |
|---|---|---|---|---|---|---|
| 1 | DCM | 1.00 | 1.0 | 0.60 | 9.0 | NA |
| 2 | DCM | 0.80 | 0.8 | 0.71 | 11.0 | NA |
| 3 | DCM | 0.60 | 0.6 | 0.87 | 13.6 | NA |
| 4 | DCM | 0.50 | 0.5 | 0.98 | 15.3 | NA |
| 5 | Toluene | 1.00 | 1.0 | 0.60 | 9.0 | NA |
| 6 | Toluene | 0.80 | 0.8 | 0.71 | 11.0 | NA |
| 7 | Toluene | 0.60 | 0.6 | 0.87 | 13.6 | NA |
| 8 | Toluene | 0.50 | 0.5 | 0.98 | 15.3 | NA |
| 9 | $Et_2O$ | 1.00 | 1.0 | 0.52 | 8.0 | 80 |
| 10 | $Et_2O$ | 1.50 | 1.0 | 0.39 | 6.0 | 50 |
| 11 | $Et_2O$ | 2.00 | 1.0 | 0.31 | 5.0 | 20 |
| 12 | $Et_2O$ | 1.25 | 0.5 | 0.52 | 8.0 | 85 |
| 13 | $Et_2O$ | 1.25 | 0.6 | 0.50 | 7.9 | 85 |

Extraction condition: Aq. NaOH solution (0.001N).

Figure 8:
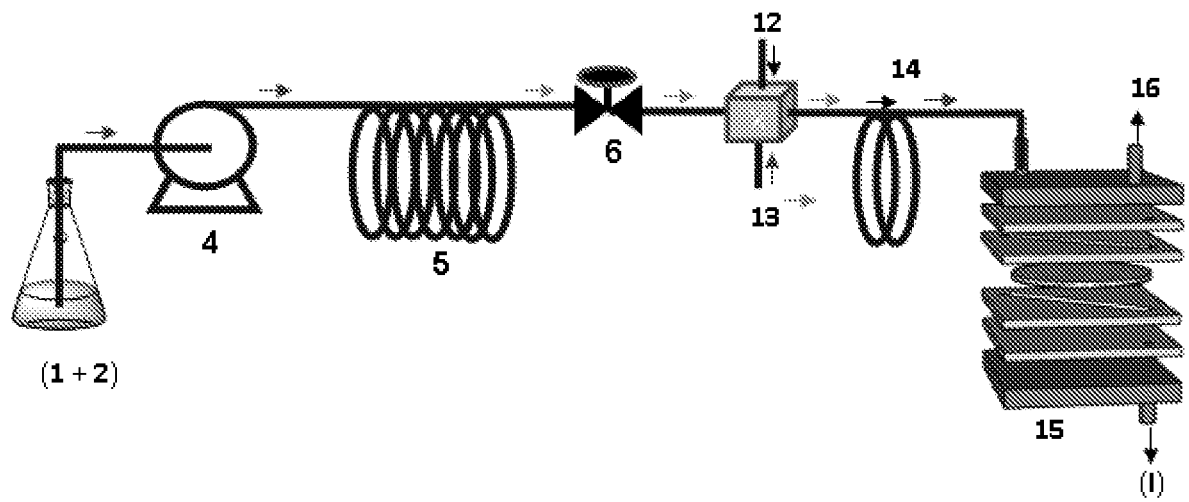
FIG. 8: Illustration of the continuous integrated flow pyrazoles synthesis, extraction and separation platform.

FIG. 8 is an illustration of the continuous integrated flow pyrazoles synthesis, extraction and separation platform; wherein the meaning of the components numbered in figure is same as described above. Present illustration describes, a time-efficient, μ-TPS for real-time for the preparation of compound of Formula (I) by reacting substituted di ketone of Formula (1) and 4-hydrazinylbenzenesulfonamide hydrochloride (2). The integrated continuous manufacturing platform produces on-demand pyrazoles with excellent yields.

Figure 9:
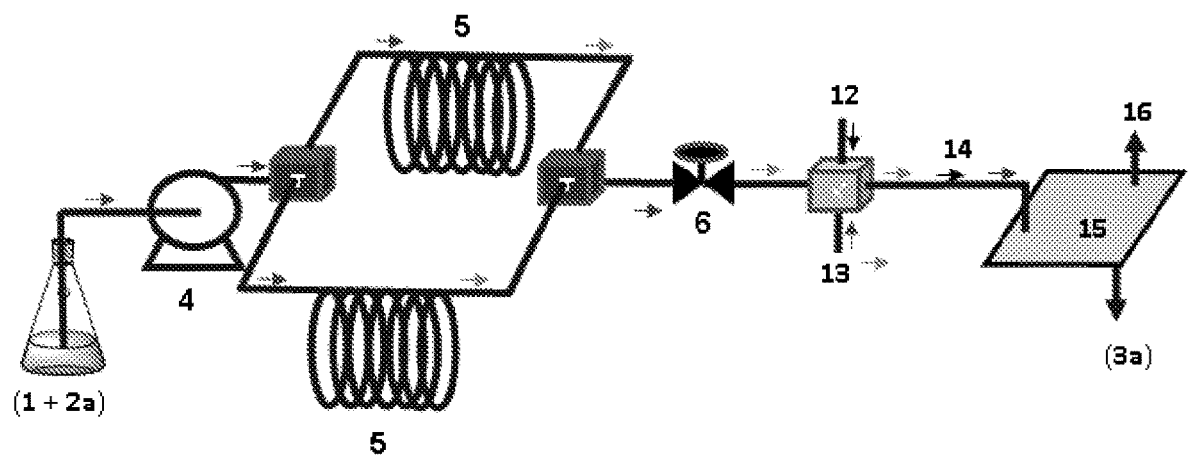
FIG. 9: Illustration of the continuous integrated flow bulk scale celecoxib's synthesis, analysis, extraction and separation platform.

FIG. 9 is an illustration of the continuous integrated flow bulk scale celecoxib's synthesis, analysis, extraction and separation platform; wherein the meaning of the components numbered in figure is same as described above. The scale-out synthesis of celecoxib (3a) using two mico-reactors (5) parallelized by the SS tubing in stack is described. The parallelized SS tubing mico-reactors are heated to maintain the desired temperature. The optimum conditions for each reactor are given according to the above identified parameters, namely, a solution of compound of Formula (2a) and hydrazine compound of Formula (1) are pumped to each reactor with the flow rate of about 1.2 mL/min and the reaction temperature is set at about 120° C. and pressure at about 32 bar. Operating the parallel reactors for 12 h with the same reaction conditions produces Celecoxib in bulk.

List of Abbreviations
BPR=Back pressure regulator
DCM=Dichloromethane
ETFE=Ethylene tetrafluoroethylene
GC=Gas chromatography
HPLC=High pressure Liquid chromatography
HRMS=High resolution mass spectroscopy
ID=Inner Diameter
IR=Infra-red
MSD=Multiple Spark Discharge
NMR=Nuclear Magnetic resonance
OD=Outer Diameter
PE=Polyethylene
PFA=Perfluoroalkoxy alkane
PTFE=Polytetrafluoroethylene
SS=Stainless Steel
TLC=Thin layer chromatography
UV=Ultra-Violet Material and Method Used in Experiments Most of the reagents and chemicals bought from Spectrochem, AVRA and Sigma-Aldrich, which were used as such without any further purification. Common organic chemicals and salts were purchased from AVRA chemicals, India.

Deionized water (18.2 mS conductivity) was used in all experiments. All work-up and purification procedures were carried out with reagent-grade solvents. Analytical thin-layer chromatography (TLC) was performed using analytical chromatography silica gel 60 F254 pre-coated plates (0.25 mm). The developed chromatogram was analysed by UV lamp (254 nm).

PTFE (id=100-800 μm) tubing, T-junction and back-pressure controller (BPR) were procured from Upchurch IDEX HEALTH & SCIENCE. Pump purchased from KNAUER. SS318 capillary bought from the spectrum market, Mumbai, India. Heating reactor bought from the Thales Nano Nanotechnology, Inc.

Measurement Method

High-resolution mass spectra (HRMS) were obtained from a JMS-T100TD instrument (DART) and Thermo Fisher Scientific Exactive (APCI).

Nuclear magnetic resonance (NMR) spectra were recorded on a Bruker 600, 500, 400 or 300 MHz in $CDCl_3$ or DMSO-$d_6$ solvent. Chemical shifts for $^1H$ NMR are expressed in parts per million (ppm) relative to tetramethylsilane (δ0.00 ppm). Chemical shifts for $^{13}C$ NMR are expressed in ppm relative to $CDCl_3$ (δ77.0 ppm). Data are reported as follows: chemical shift, multiplicity (s=singlet, d=doublet, dd=doublet of doublets, t=triplet, q=quartet, quin=quintet, sext=sextet, m=multiplet), coupling constant (Hz), and integration.

GC/MS analysis was conducted on Shimadzu technology GCMS-QP2010 instrument equipped with a HP-5 column (30 m×0.25 mm, Hewlett-Packard) and inbuilt MS 5975C VL MSD system with triple axis detector. ATR analysis was conducted on Portable FTIR spectrometer Bruker ALPHA.

EXAMPLES

General Procedure for the Synthesis of Pyrazoles of Formula (I)

1. A solution containing reactants and solvent under stoichiometric molar ratios of [2a-2i/1/MeOH/$H_2O$] was taken in bottle and connected with pump as described in FIG. 8.
2. The reactant mixture containing the above solution was introduced into a SS-tubing (id=1000 μm, length=10 meter, heat 120° C.) for the synthesis of pyrazoles during 13.2 min of residence time and 32 bar pressure.
3. In next step, reaction mixture was basified and solvent exchange (from hydrophilic solvent to low boiling hydrophobic solvent such as DCM, toluene, and diethyl ether) was done by introducing basic water and low boiling solvent through additional X-mixer to form organic-aqueous droplets. The organic-aqueous droplets were passed through the micro-separator.

Example 1

Synthesis of 4-(5-p-tolyl-3-(trifluoromethyl)-1H-pyrazol-1-yl) benzene sulfonamide (3a, Celecoxib)

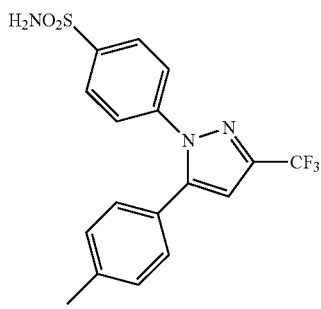 [SMILES: Cc1ccc(-c2cc(C(F)(F)F)nn2-c2ccc(S(N)(=O)=O)cc2)cc1]

A reactor coil (SS316 tubing id=1 mm, 10 meter, volume=8 mL) was assembled and joined to the other components of the continuous flow system to ensure efficient mixing. The stock solution was prepared in a 500 mL volumetric flask under anhydrous condition before injecting into stainless steel 8 mL reactor through a HPLC pump. The stock solution containing a mixture of 4,4,4-trifluoro-1-p-tolylbutane-1,3-dione (2a) (1.0 g, 4.34 mmol, 1.00 equiv) and hydrazinylbenzenesulfonamide hydrochloride (1) (969 mg, 4.34 mmol, 1.00 equiv) in 365 mL of methanol and 35 mL of water was passed through the pre-heated 120° C. SS316-tube reactor (8 mL), keeping 13.3 min. residence time and 32 bar pressure. Finally out-flowing product mixture was quenched and solvent exchange was done from MeOH: water to low boiling solvent diethyl ether by introducing aq. NaOH through an additional X-mixer to form organic-aqueous droplets. Complete extraction between the organic-aqueous segments was observed after 0.5 min retention time achieved by flowing through a PTFE capillary ((id=1000 μm, length=2.6 m, vol.=2 mL). Further, organic-aqueous segment was separated by passing through micro separator of present invention and complete separation was achieved by regulating the back pressures and retention time (5.6 sec) along with the flow rate of diethyl ether (1200 μmin) and aq. NaOH (0.6 μl/min). Extracted waste water layer was further extracted with diethyl ether and analyzed by LC-MS, which showed no traces of product and was again confirmed by absence of the corresponding peaks in crude NMR analysis ($^1$H and $^{13}$C NMR spectra). The organic extract (diethyl ether layer) was concentrated and the resulting residue was purified by silica gel column chromatography (hexane/ethyl acetate; 60:40) to provide an off-white solid (3a) (411 mg, 85%), Melting point: 152° C. The spectra data matched with values reported in the literature (Tetrahedron Letters, 54(49), 6682-6686; 2013; Organic Process Research & Development 2009, 13, 98-101).

$^1$H NMR (400 MHz, DMSO) δ7.88 (d, J=8.7 Hz, 2H), 7.57-7.53 (m, 2H), 7.52 (s, 2H), 7.22 (d, J=2.8 Hz, 3H), 7.20 (s, 1H), 2.32 (s, 3H);

$^{19}$F NMR (376 MHz, CDCl$_3$) δ-56.119 (s);

$^{13}$C NMR (101 MHz, DMSO) δ145.27, 144.00, 142.18 (q, J=38.38 Hz), 141.12, 139.11, 129.42, 128.78, 126.81, 126.00, 125.36, 121.18 (q, J=270.68 Hz), 106.64, 21.30;

IR ($v_{max}$): 3503, 3357, 3267, 3109, 1601, 1484, 1466, 1409, 1340, 1277, 1238, 1164, 979, 908, 839, 812, 761 cm$^{-1}$;

HRMS (ESI); m/z calcd for C$_{17}$H$_{14}$F$_3$N$_3$O$_2$S [M+H]$^+$: 382.0837, found: 382.0843.

Example 2: Synthesis of 4-(5-phenyl-3-(trifluoromethyl)-1H-pyrazol-1-yl) benzene sulfonamide (3b)

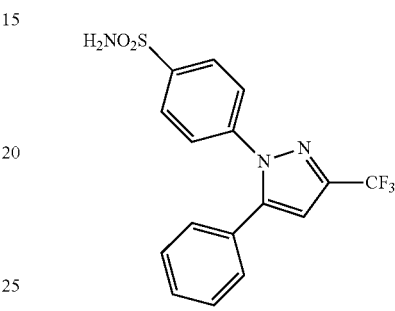

Compound of Formula (3b) was synthesised following the procedure described above under Example 1 and general procedure involving corresponding reactants of formula (2b). Off-white solid (63.8 mg, 75%); Melting point: 146-148° C. The spectra data matched with values reported in the literature (Bioorganic & Medicinal Chemistry, 22(8), 2529-2534; 2014).

$^1$H NMR (400 MHz, DMSO) δ7.88 (d, J=8.7 Hz, 2H), 7.55 (d, J=8.7 Hz, 2H), 7.52 (s, 2H), 7.43 (dd, J=5.0, 2.1 Hz, 2H), 7.34 (d, J=1.7 Hz, 1H), 7.26 (s, 1H).

$^{13}$C NMR (101 MHz, DMSO) δ145.71, 144.40, 142.69 (q, J=37.37 Hz), 141.52, 132.30, 129.93, 129.41, 129.36, 128.72, 127.29, 126.52, 126.04, 121.54 (q, J=269.67 Hz), 106.91.

IR ($v_{max}$): 3588, 3364, 3270, 3108, 1594, 1484, 1461, 1336, 1278, 1237, 1159, 975, 908, 840, 761, 693 cm$^{-1}$;

HRMS (ESI); m/z calcd for C$_{16}$H$_{12}$F$_3$N$_3$O$_2$S [M+H]$^+$: 368.0681, found: 368.0679.

Example 3

Synthesis of 4-(5-(4-fluorophenyl)-3-(trifluoromethyl)-1H-pyrazol-1-yl) benzene sulfonamide (3c, Mavacoxib)

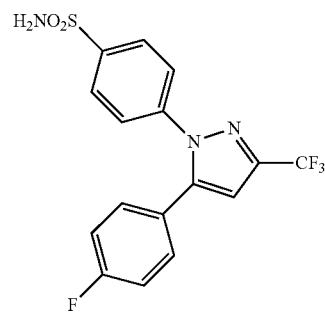 [SMILES: NS(=O)(=O)c1ccc(-n2nc(C(F)(F)F)cc2-c2ccc(F)cc2)cc1]

Compound of Formula (3c) was synthesised following the procedure described above under Example 1 and general procedure involving corresponding reactants of formula (2c). Off-white solid (270 mg, 82%); Melting point: 160-162° C.; The spectra data matched with values reported in the literature (*European Journal of Organic Chemistry*, 2017 (44), 6566-6574, 2017).

$^1$H NMR (400 MHz, DMSO) δ7.88 (d, J=8.7 Hz, 2H), 7.55 (d, J=8.7 Hz, 2H), 7.52 (s, 2H), 7.42-7.37 (m, 2H), 7.30 (d, J=8.9 Hz, 2H), 7.26 (s, 1H).

$^{13}$C NMR (101 MHz, DMSO) δ164.00, 162.03, 144.73, 144.45, 142.63 (q, J=30.3 Hz), 141.36, 131.92, 131.85, 127.33, 126.51, 125.25, 121.62 (q, J=216.14 Hz), 116.54, 116.33, 107.08;

IR ($v_{max}$): 3268, 3099, 1601, 1556, 1465, 1409, 1338, 1277, 1234, 1158, 976, 906, 840, 759 cm$^{-1}$;

HRMS (ESI); m/z calcd for $C_{16}H_{11}F_4N_3O_2S$ [M+H]$^+$: 386.0586, found: 368.0586.

Example 4

Synthesis of 4-(5-(4-chlorophenyl)-3-(trifluoromethyl)-1H-pyrazol-1-yl) benzene sulfonamide (3d)

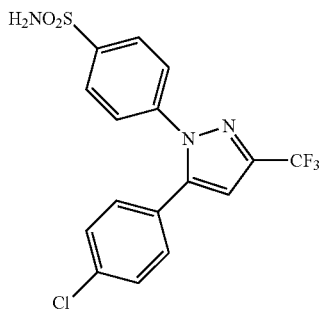

Compound of Formula (3d) was synthesised following the procedure described above under Example 1 and general procedure involving corresponding reactants of formula (2d). White solid (360 mg, 75%); Melting point: 138-140° C. The spectra data matched with values reported in the literature (U.S. Pat. No. 6,492,411).

$^1$H NMR (400 MHz, DMSO) δ7.92-7.87 (m, 2H), 7.59-7.55 (m, 2H), 7.54-7.49 (m, 4H), 7.39-7.34 (m, 2H), 7.30 (s, 1H);

$^{13}$C NMR (101 MHz, DMSO) δ144.58, 144.18, 142.87 (q, J=38.38 Hz), 141.34, 134.89, 131.13, 129.41, 127.38, 126.56, 121.29 (q, J=269.67 Hz), 107.00;

IR ($v_{max}$): 3492, 3330, 3272, 3100, 1598, 1557, 1461, 1408, 1339, 1275, 1236, 1611, 1099, 977, 906, 839, 760 cm$^{-1}$;

HRMS (ESI); m/z calcd for $C_{16}H_{11}ClF_3N_3O_2S$ [M+H]$^{30}$ : 402.0291, found: 402.0291.

Example 5

Synthesis of 4-(5-(4-bromophenyl)-3-(trifluoromethyl)-1H-pyrazol-1-yl) benzene sulfonamide (3e)

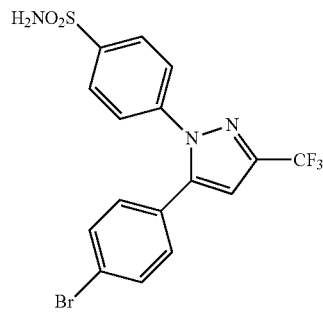 [SMILES: NS(=O)(=O)c1ccc(-n2nc(C(F)(F)F)cc2-c2ccc(Cl)cc2)cc1]

Compound of Formula (3e) was synthesised following the procedure described above under Example 1 and general procedure involving corresponding reactants of formula (2e). The compound was further purified by silica gel column chromatography (hexane/ethyl acetate; 70:30) to provide a white solid (196.6 mg, 65%); Melting point: 132-134° C. The spectra data matched with values reported in the literature (Angewandte Chemie, International Edition, 56 (12), 3354-3359; 2017).

$_1$H NMR (400 MHz, CDCl$_3$) δ7.93 (d, J=8.8 Hz, 2H), 7.50 (dd, J=24.8, 8.6 Hz, 4H), 7.11 (d, J=8.6 Hz, 2H), 6.78 (s, 1H), 5.04 (s, 2H).

$^{13}$C NMR (101 MHz, CDCl$_3$) δ144.57, 143.90, 141.74 (q, J=37.37 Hz), 141.29, 132.34, 131.48, 127.94, 127.39, 126.54, 124.68, 121.14 (q, J=269.67 Hz), 107.19;

IR ($v_{max}$): 3545, 3275, 3096, 1596, 1555, 1458, 1405, 1339, 1273, 1234, 1158, 1015, 977, 904, 834, 757 cm$^{-1}$;

HRMS (ESI); m/z calcd for $C_{16}H_{11}BrF_3N_3O_2S$ [M+H]$^+$: 444.9786, found: 444.9778.

Example 6

Synthesis of 4-(5-(4-methoxyphenyl)-3-(trifluoromethyl)-1H-pyrazol-1-yl) benzene sulfonamide (3f)

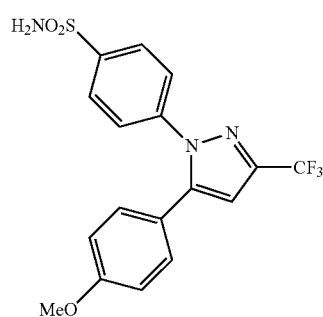 [SMILES: COc1ccc(-c2cc(C(F)(F)F)nn2-c2ccc(S(N)(=O)=O)cc2)cc1]

Compound of Formula (3f) was synthesised following the procedure described above under Example 1 and general procedure involving corresponding reactants of formula (20.

The compound was further purified by silica gel column chromatography (hexane/ethyl acetate; 60:40) to provide a white solid (516 mg, 79%); Melting point: 142-144° C. The spectra data matched with values reported in the literature (U.S. Patent Application No. 2009/0111799).

$^1$H NMR (400 MHz, DMSO) δ7.88 (d, J=8.6 Hz, 2H), 7.55 (dd, J=11.5, 4.7 Hz, 4H), 7.29-7.23 (m, 2H), 7.16 (s, 1H), 7.01-6.95 (m, 2H), 3.78 (s, 3H).

$^{13}$C NMR (101 MHz, DMSO) δ160.42, 145.61, 144.37, 142.62 (q, J=37.57 Hz), 141.67, 130.83, 127.30, 126.45, 121.80, 114.80, 106.36, 55.75;

IR ($v_{max}$): 3547, 3268, 3099, 1608, 1562, 1466, 1408, 1339, 1242, 1161, 1027, 975, 906, 838, 758 cm$^{-1}$;

HRMS (ESI); m/z calcd for $C_{17}H_{14}F_3N_3O_3S$ [M+H]$^+$: 398.0786, found: 398.0787

Example 7

Synthesis of 4-(5-(biphenyl-4-yl)-3-(trifluoromethyl)-1H-pyrazol-1-yl) benzene sulfonamide (3g)

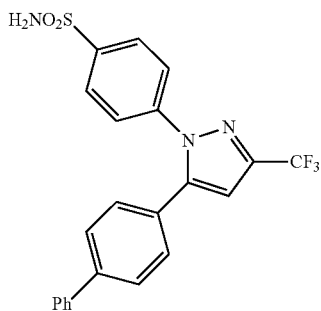 [SMILES: NS(=O)(=O)c1ccc(-n2nc(C(F)(F)F)cc2-c2ccc(-c3ccccc3)cc2)cc1]

Compound of Formula (3g) was synthesised following the procedure described above under Example 1 and general procedure involving corresponding reactants of formula (2g). The compound was further purified by silica gel column chromatography (hexane/ethyl acetate; 60:40) to provide a white solid (243 mg, 80%); Melting point: 152-154° C. The spectra data matched with values reported in the literature. (U.S. Patent Application No. 20090111799).

1H NMR (400 MHz, DMSO) δ8.12-8.00 (m, 1H), 7.90 (t, J=9.7 Hz, 2H), 7.86-7.79 (m, 1H), 7.74 (dd, J=13.9, 7.9 Hz, 4H), 7.66-7.58 (m, 2H), 7.49 (dd, J=16.7, 9.1 Hz, 3H), 7.42 (t, J=7.5 Hz, 2H), 7.32 (s, 1H).

$^{13}$C NMR (101 MHz, DMSO) δ151.76, 145.34, 144.60, 142.11 (q, J=37.37 Hz), 139.29, 129.93, 129.53, 128.52, 126.73, 126.58, 123.12, 120.51 (q, J=270.68 Hz), 108.36, 107.01;

IR ($v_{max}$): 3347, 3269, 3082, 1596, 1459, 1404, 1338, 1282, 1233, 1156, 976, 905, 840, 757, 695 cm$^{-1}$;

HRMS (ESI); m/z calcd for $C_{22}H_{16}N_3O_2F_3S$ [M+H]$^+$: 444.0994, found: 444.0993.

Example 8

Synthesis of 4-(5-(4-nitrophenyl)-3-(trifluoromethyl)-1H-pyrazol-1-yl) benzene sulfonamide (3h)

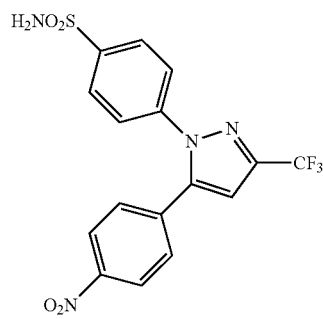 [SMILES: NS(=O)(=O)c1ccc(-n2nc(C(F)(F)F)cc2-c2ccc([N+](=O)[O-])cc2)cc1]

Compound of Formula (3h) was synthesised following the procedure described above under Example 1 and general procedure involving corresponding reactants of formula (2h). The compound was further purified by silica gel column chromatography (hexane/ethyl acetate; 60:40) to provide a white solid (595 mg, 78%); Melting point: 146-148° C. The spectra data matched with values reported in the literature (Bioorganic & Medicinal Chemistry Letters, 20(15), 4544-4549; 2010).

$^1$H NMR (500 MHz, DMSO) δ8.43-8.32 (m, 1H), 8.27 (d, J=8.7 Hz, 2H), 8.09-8.01 (m, 1H), 8.10-7.98 (m, 2H), 7.90 (d, J=8.4 Hz, 4H), 7.61 (dd, J=13.8, 8.8 Hz, 2H), 7.54 (s, 1H), 7.47 (s, 1H).

$^{13}$C NMR (126 MHz, DMSO) δ148.16, 144.82, 143.63, 142.88 (q, J=37.80 Hz), 141.08, 134.98, 130.84, 127.49, 127.19, 126.90, 126.61, 124.79, 121.58 (q, J=275.94 Hz), 118.73, 108.23;

IR ($v_{max}$): 3491, 3263, 3085, 1599, 1562, 1519, 1460, 1407, 1343, 1284, 1236, 1158, 976, 905, 847, 757.05, 703 cm$^{-1}$;

HRMS (ESI); m/z calcd for $C_{16}H_{11}F_3N_4O_4S$ [M+H]$^+$: 413.0531, found: 413.0527.

Example 9

Synthesis of 4-(5-(thiophen-2-yl)-3-(trifluoromethyl)-1H-pyrazol-1-yl) benzenesulfonamide (3i)

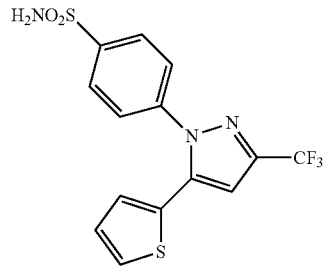 [SMILES: NS(=O)(=O)c1ccc(-n2nc(C(F)(F)F)cc2-c2cccs2)cc1]

Compound of Formula (3i) was synthesised following the procedure described above under Example 1 and general procedure involving corresponding reactants of formula (2i). The compound was further purified by silica gel column chromatography (hexane/ethyl acetate; 70:30) to provide a white solid (383 mg, 76%); Melting point: 200-202° C. The spectra data matched with values reported in the literature (Medicinal Chemistry Research, 24, 2632-2644, 2015).

$^1$H NMR (400 MHz, DMSO) δ7.96 (d, J=8.5 Hz, 2H), 7.77-7.63 (m, 3H), 7.58 (s, 2H), 7.35 (s, 1H), 7.23 (dd, J=3.6, 1.1 Hz, 1H), 7.13 (dd, J=5.0, 3.7 Hz, 1H).

$^{13}$C NMR (101 MHz, DMSO) δ145.43, 142.60 (q, J=38.38 Hz), 141.17, 139.82, 130.03, 129.80, 128.63, 128.36, 127.57, 127.39, 121.61 (q, J=275.73 Hz), 106.48;

IR ($v_{max}$): 3342, 3214, 3102, 1480, 1342, 1242, 1155, 976, 907, 842, 769, 718, 675 cm$^{-1}$;

HRMS (ESI); m/z calcd for $C_{14}H_{10}F_3N_3O_2S_2$ [M+H]$^+$: 374.0245, found: 374.0244.

Bulk Scale Synthesis of Compound of Formula 3a:
1. A two-reactor coil (vol.=16 mL) was assembled and joined to the other components of the continuous flow system to ensure efficient mixing (FIG. 9).
2. The feed solution was prepared in a 500 mL volumetric flask under anhydrous condition before injected into stainless steel 8 mL reactor through a pump.
3. The feed solution containing a mixture of 4,4,4-trifluoro-1-p-tolylbutane-1,3-dione (2a) (4.34 mmol, 1.0 equiv.) and hydrazinylbenzenesulfonamide hydrochloride (1) (4.34 mmol, 1.00 equiv) in 365 mL Methanol and 35 mL water.
4. The pump was set to infuse at 1.2 mL min$^{-1}$ (total flow rate=1.2 mL min$^{-1}$).
5. The solution was passed through the integrated continuous flow system to obtain compound of Formula 3a (Celecoxib).

SIGNIFICANCE OF THE WORK CARRIED OUT

In view of the importance and limitations of efficient scalable production methods for the preparation of celecoxib and related analogs, the present process of continuous micro total process system serves as a highly effective, improved and scalable production method for the synthesis of celecoxib and analogs of Formula (I).

ADVANTAGES OF THE INVENTION

The various advantages of the present process are given below:
1. The main advantage of the present invention is that it provides an efficient process for the preparation of celecoxib in continuous micro total process system.
2. The advantage of the present invention is that the process could be operated in continuous flow method in bulk scale.
3. Another advantage of the present invention is the employment of easily tunable process having simpler reaction parameters.
4. Extraction and wastage removal of the products is inbuilt and straightforward.
5. This is a fully automated and highly economical method for the production of celecoxib and analogs of Formula (I).
6. Further advantage of the invention is employment of polymer (Teflon) micro-separator design, which is base, solvent and heat resistant.
7. Another advantage of the process involves easy scale-up using parallel stacking.

The invention claimed is:
1. A continuous flow micro-total process for the preparation of celecoxib or a celecoxib analog, wherein the celecoxib or the celecoxib analog is a compound according to formula (I):

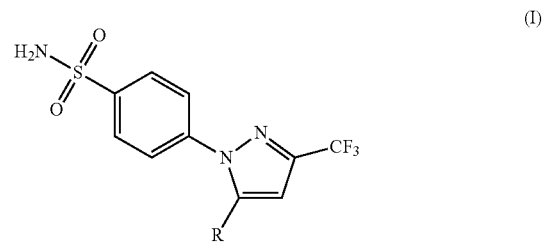

where R is a phenyl or heterocyclic group, wherein the phenyl or heterocyclic group is substituted with one or more substituents selected from halogen, hydroxy, alkoxy, aldehyde, carboxylic acid, nitro, alkyl, amino, thiol, and ester, the process comprising:
(i) introducing a solution of reactants of formula (1) and formula (2):

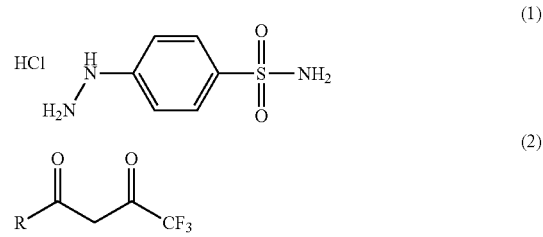

in a protic solvent and water to a micro-reactor through a pump to obtain a reaction mixture, where R of formula (2) is as defined in formula (I);
(ii) maintaining the reaction mixture of (i) in the micro-reactor for about 10 minutes to about 30 minutes at a temperature of about 80° C. to about 130° C. and at a pressure of about 25 bar to about 35 bar to synthesize the compound of formula (I) in the reaction mixture;
(iii) introducing a basifying agent and an extraction solvent to the reaction mixture of (ii) through an X junction to form organic-aqueous droplets having organic and aqueous segments;
(iv) separating the organic and aqueous segments by passing the organic-aqueous droplets of (iii) through an extraction section followed by a micro-separator comprising a metal holder, a metal protecting PTFE or PE film, a spiral polymer-based channel, and a polypropylene coated PTFE porous thin film membrane, in the presence of an extraction solvent system;
(v) removing organic solvents to obtain the compound of formula (I); and
(vi) optionally, purifying the compound of formula (I).

2. The process of claim 1, wherein the compound of formula (I) is selected from the group consisting of
4-(5-p-tolyl-3-(trifluoromethyl)-1H-pyrazol-1-yl)benzene sulfonamide,
4-(5-phenyl-3-(trifluoromethyl)-1H-pyrazol-1-yl)benzene sulfonamide,
4-(5-(4-fluorophenyl)-3-(trifluoromethyl)-1H-pyrazol-1-yl)benzene sulfonamide, 4-(5-(4-chlorophenyl)-3-(trifluoromethyl)-1H-pyrazol-1-yl)benzene sulfonamide,
4-(5-(4-bromophenyl)-3-(trifluoromethyl)-1H-pyrazol-1-yl)benzene sulfonamide,
4-(5-(4-methoxyphenyl)-3-(trifluoromethyl)-1H-pyrazol-1-yl)benzene sulfonamide,
4-(5-(biphenyl-4-yl)-3-(trifluoromethyl)-1H-pyrazol-1-yl)benzene sulfonamide,
4-(5-(4-nitrophenyl)-3-(trifluoromethyl)-1H-pyrazol-1-yl)benzene sulfonamide, and
4-(5-(thiophen-2-yl)-3-(trifluoromethyl)-1H-pyrazol-1-yl)benzene sulfonamide.

3. The process of claim 1, wherein the reactant of formula (2) is selected from the group consisting of
4,4,4-trifluoro-1-(p-tolyl)butane-1,3-dione,
4,4,4-trifluoro-1-phenylbutane-1,3-dione,
4,4,4-trifluoro-1-(4-fluorophenyl)butane-1,3-dione,
1-(4-chlorophenyl)-4,4,4-trifluorobutane-1,3-dione,
1-(4-bromophenyl)-4,4,4-trifluorobutane-1,3-dione,
4,4,4-trifluoro-1-(4-methoxyphenyl)butane-1,3-dione,
1-([1,1'-biphenyl]-4-yl)-4,4,4-trifluorobutane-1,3-dione,
4,4,4-trifluoro-1-(4-nitrophenyl)butane-1,3-dione, and
4,4,4-trifluoro-1-(thiophen-2-yl)butane-1,3-dione.

4. The process of claim 1, wherein the protic solvent in (i) is an alcoholic solvent selected from the group consisting of methanol, ethanol, isopropanol, n-butanol, t-butanol, and mixtures thereof.

5. The process of claim 1, wherein the basifying agent in (iii) is an inorganic base selected from KOH, $Na_2CO_3$, $NaHCO_3$, and mixtures thereof.

6. The process of claim 1, wherein the extraction solvent is a hydrophobic solvent selected from dichloroethane, chloroform, dichloromethane, dimethyl ether, diethyl ether, isopropyl ether, toluene, mesitylene, xylene, hexane, and mixtures thereof.

7. The process of claim 1, wherein a continuous flow micro-total process system is employed for the bulk scale preparation the compound of formula (I).

8. The process of claim 2, wherein:
the compound of formula (I) is 4-(5-p-tolyl-3-(trifluoromethyl)-1H-pyrazol-1-yl)benzene sulfonamide of formula (3a):

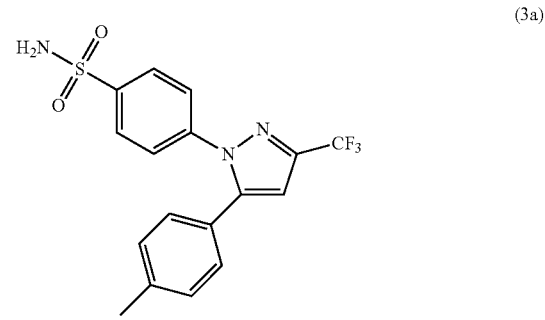 [SMILES: Cc1ccc(-c2cc(C(F)(F)F)nn2-c2ccc(S(N)(=O)=O)cc2)cc1]

(3a)

the reactant of formula (2) is 4,4,4-trifluoro-1-p-tolylbutane-1,3-dione;
the solution introduced to the micro-reactor in (i) has a molar ratio of 1 part reactant of formula (1) to 1 part reactant of formula (2) to 277 parts protic solvent to 45 parts water; and
the protic solvent is methanol.

9. The process of claim 8, wherein the basifying agent is an aqueous NaOH solution and the extraction solvent is diethyl ether.

* * * * *